United States Patent [19]

Bedi et al.

[11] Patent Number: 5,248,298
[45] Date of Patent: Sep. 28, 1993

[54] INSERT FOR SHIELDED TROCAR

[75] Inventors: James Bedi, Cincinnati, Ohio; Steven Annunziato, Fords, N.J.

[73] Assignee: Ethicon, Inc., Somerville, N.J.

[21] Appl. No.: 869,673

[22] Filed: Apr. 16, 1992

Related U.S. Application Data

[63] Continuation of Ser. No. 6727,798, Dec. 14, 1992, abandoned.

[51] Int. Cl.$^5$ .............................................. A61M 31/00
[52] U.S. Cl. ......................................... 604/51; 604/264
[58] Field of Search ............... 604/263, 31, 46, 51, 604/164, 165, 171, 110; 606/181, 182, 108, 185, 172, 184; 128/753, 754

[56] References Cited

U.S. PATENT DOCUMENTS

| | | | |
|---|---|---|---|
| 4,203,446 | 5/1980 | Hofert et al. | |
| 4,230,123 | 10/1980 | Hawkin | 128/658 |
| 4,535,773 | 8/1985 | Yoon | 604/51 |
| 4,601,710 | 7/1986 | Moll | 604/165 |
| 4,654,030 | 3/1987 | Moll et al. | 604/165 |
| 4,655,750 | 4/1987 | Vaillancourt | 604/165 |
| 4,838,282 | 6/1989 | Strasser et al. | 128/754 |
| 4,869,717 | 9/1989 | Adair | 604/51 |
| 4,902,280 | 2/1990 | Lander | 604/165 |
| 4,931,042 | 6/1990 | Holmes et al. | 604/164 |
| 4,973,313 | 11/1990 | Katsaros et al. | 604/165 |
| 5,066,288 | 11/1991 | Deniega et al. | 604/274 |

FOREIGN PATENT DOCUMENTS 0265193 4/1988 European Pat. Off. ............ 606/185

Primary Examiner—C. Fred Rosenbaum
Assistant Examiner—Vanitha Alexander
Attorney, Agent, or Firm—Paul J. Coletti

[57] ABSTRACT

An insert is provided to be attached to a shield on a surgical trocar obturator handle. The insert is actuated by the surgical trocar cannula handle so that it causes the shield to expose the sharpened obturator tip after insertion of the obturator and shield within the cannula. After usage, the insert is deactivated so that the shield again covers the obturator. The obturator can then be removed from the cannula handle and obturator shield, and the obturator handle can be discarded safely.

7 Claims, 4 Drawing Sheets

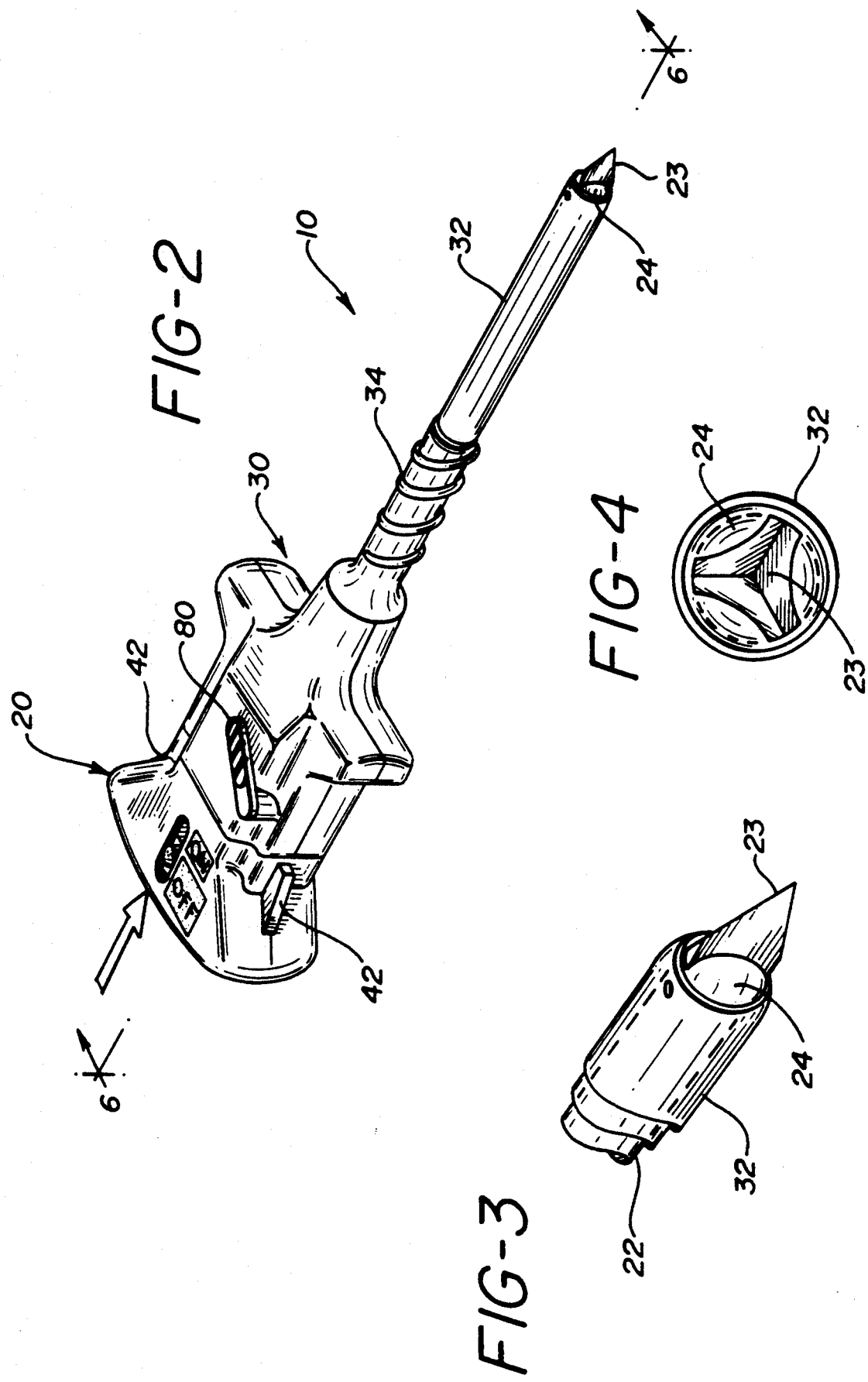

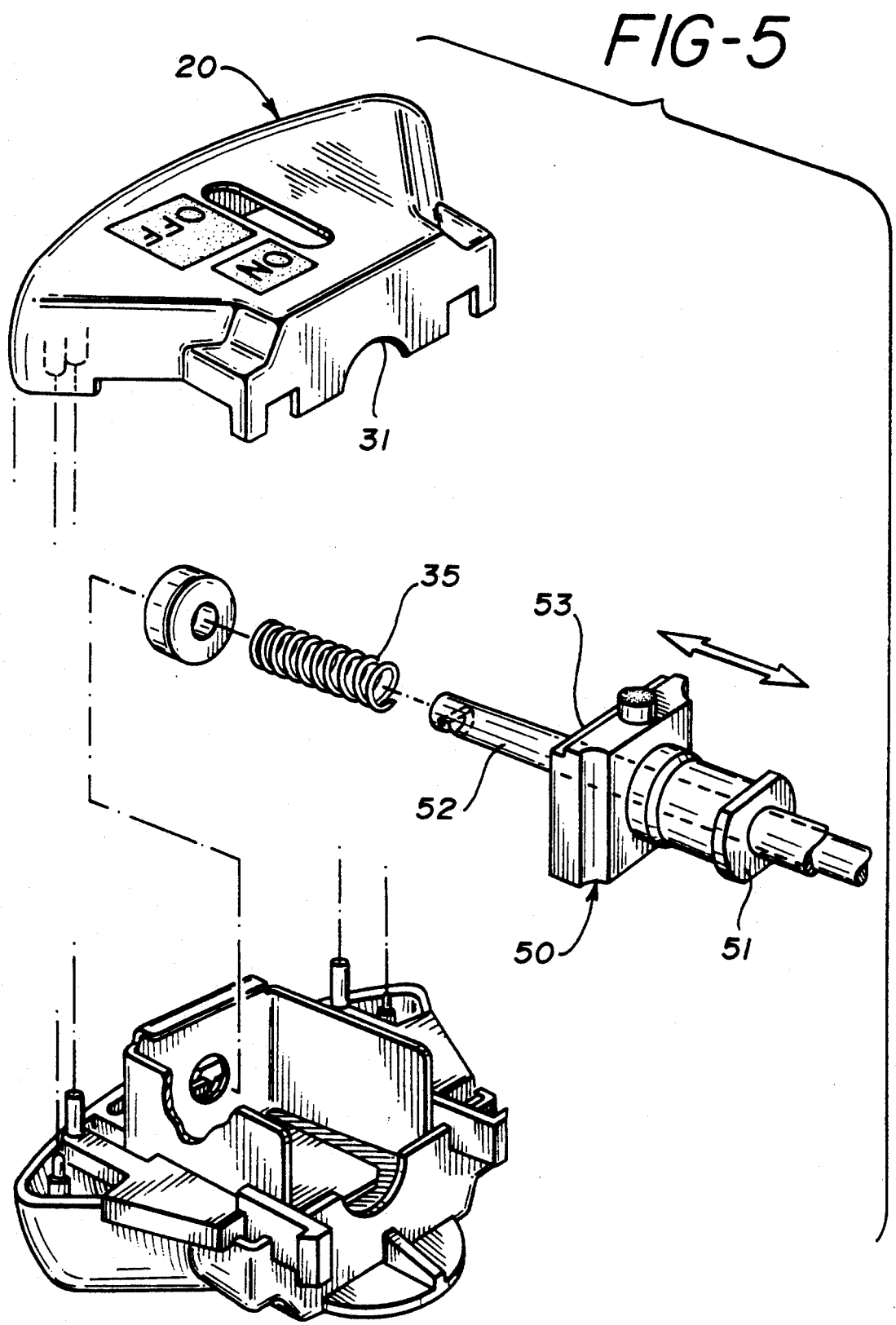

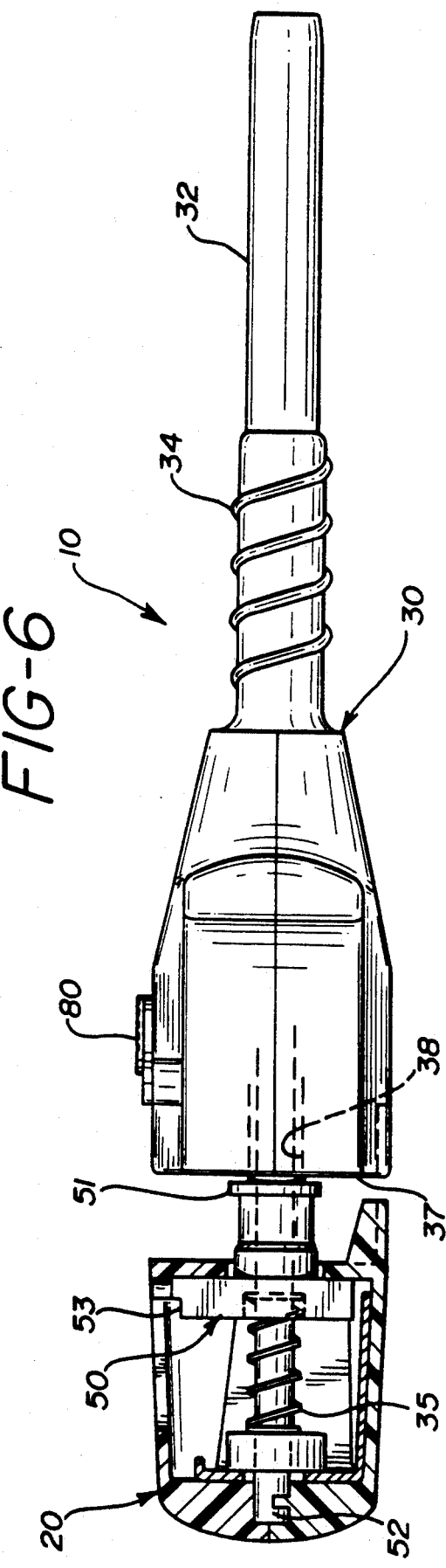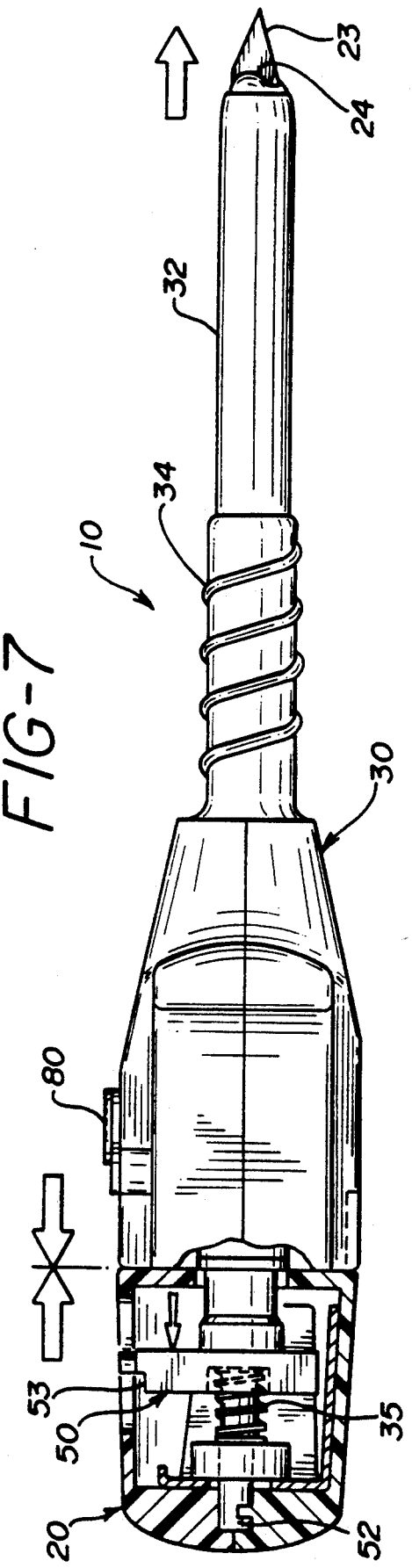

INSERT FOR SHIELDED TROCAR

This is a continuation, of application Ser. No. 627,798, filed Dec. 14, 1992, which is hereby incorporated by reference now abandoned May 6, 1992.

FIELD OF THE INVENTION

This invention relates to trocars used to puncture tissue to enable the performance of laparoscopic or arthroscopic surgery. In particular, the invention relates to such trocars which employ a safety device to shield the obturator point immediately after the point has perforated tissue.

BACKGROUND OF THE INVENTION

A trocar generally comprises two major components, a trocar tube and an obturator. The trocar tube is inserted through the skin to access a body cavity. It is through the tube in which laparoscopic or arthroscopic surgery is performed. In order to penetrate the skin, the distal end of the trocar tube is placed against the body and an obturator is inserted through the tube. By pressing against the proximal end of the obturator, the point of the obturator is forced through the skin until it enters the body cavity. At this time, the trocar tube is inserted through the perforation made by the obturator. The obturator is withdrawn, leaving the trocar tube as an accessway to the body cavity.

It has been found that some resistive force is required to cause the obturator point to penetrate the skin and underlying tissue. When the point finally breaks through this tissue, resistance to penetration is suddenly removed, and the obturator point can penetrate to reach within the body cavity. To avert danger to the patient, trocars have been developed which carry a spring-loaded tubular shield within the trocar tube and surrounding the obturator. The distal end of the shield presses against the skin as the obturator point penetrates the body, until the obturator has formed a perforation with a diameter sufficient to allow the shield to pass through. At that time the resistance of the tissue to the spring-loaded shield is removed, and the shield springs forward to extend into the body cavity, surrounding the point of the obturator. Thus, the shield thus protects the internal body organs from inadvertent contact with the point of the obturator. A trocar including such a safety shield is described in U.S. Pat. No. 4,535,773, for example.

Yet, in some procedures it may be desirable to have the trocar nonshielded throughout the time when the trocar is placed within the trocar tube cannula. In this way, the user is able to slightly withdraw the trocar from the pierced tissue, and then continue piercing. This prevents what is commonly referred to as "tenting" of pneuoperitoneum. In this fashion, tenting can be reduced, and usage of trocars can adequately provide for access to the body. Also, if the trocar can be seen entering the body, for instance through an inserted scope device, any danger to the patient is avoided by closely following the path of the oburator tip with the scope.

With current shielded trocars, it is necessary to remove the cannula handle from the obturator handle to "reload" the shield on the trocar. In this fashion, therefore, it is necessary to perform an extra step while the obturator tip is inserted within pneuoperitoneum.

SUMMARY OF THE INVENTION

It is an object of the invention to provide for a safety trocar in which the obturator tip is shielded at all times until final insertion into a cannula.

It is yet another object of the invention to provide for a safety trocar in which the obturator tip is exposed throughout piercing of the skin wall and when within pneuoperitoneum.

It is yet another object to provide for the capability of the surgeon to constantly pierce within the abdominal wall throughout usage of the trocar, and yet be protected when the obturator tip is removed from a cannula after piercing.

These and other objects of the invention are provided in a shielded trocar containing an obturator tip and a safety shield which are insertable into a cannula. After insertion, the shield is actuated so that the obturator tip is exposed when the shield and obturator are fully inserted within the cannula. In this fashion, the obturator tip is then exposed through the end of the safety shield and outside the cannula. Thus, the user is able to pierce the abdominal walls, and then work within the pneuoperitoneum without the need to rearm the safety trocar every time it is desired to pierce the pneuoperitoneum. However, once the safety trocar is separated, so that the obturator tip and safety shield are removed from the cannula, the spring activated shield again covers the tip so that the obturator tip is no longer operable. Thus, the user removing the obturator tip is again protected after the obturator tip has adequately performed its function.

These and other objects of the invention are more readily understood from the attached Detailed Description of the Drawings in conjunction with the Detailed Description of the Invention.

DETAILED DESCRIPTION OF THE DRAWINGS

FIG. 2 is a perspective view of a trocar incorporating the invention after the obturator and shield have been emplaced within the cannula;

FIG. 3 is a partial cutaway perspective view of an exposed obturator tip when placed within the cannula with the shield;

FIG. 4 is a bottom view of an exposed trocar with the obturator tip projecting from the shield and cannula;

FIG. 5 is an assembly view of the obturator handle of the invention;

FIG. 6 is a plan view in partial cross-section of the invention as taken along the lines 6—6 of FIG. 2; and FIG. 7 is a view similar to FIG. 6 with the present invention being operated during the closure of the obturator handle upon the cannula handle.

DETAILED DESCRIPTION OF THE INVENTION

Figure 1:
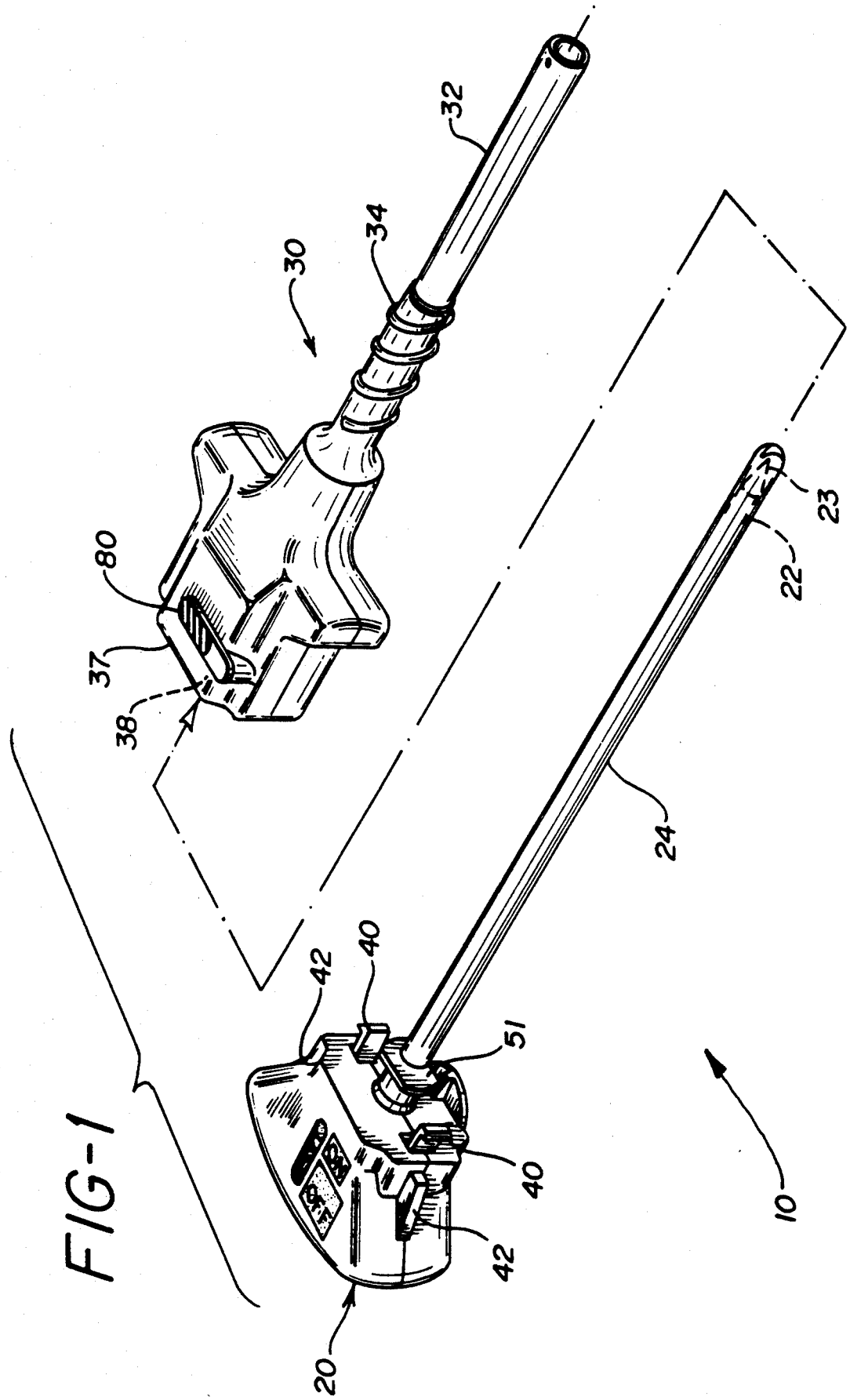
FIG. 1 is a perspective assembly view of a trocar incorporating the invention.

As seen in FIGS. 1-7, there is disclosed a safety trocar 10 which contains two major components. First, there is an obturator handle 20 seen containing an obturator 22 covered by a safety shield 24. Second, there is a cannula handle 30 containing a generally hollow tubular cannula 32. The obturator handle 20 is emplaced within the cannula 32 by placing the obturator 22 and shield 24 within the cannula handle 30, as seen in FIGS. 1 and 2.

It is to be noted that the obturator 22 has a sharpened tip 23, which when exposed is capable of piercing tissue. Generally, the shield 24 is capable of shielding the obturator tip 23 when the trocar 10 is not fully assembled. The cannula 32 connected to the cannula handle 30, when inserted fully within the abdominal cavity, is operable for usage with laparascopic instruments such as laparascopes and endoscopic clip appliers and other devices. The cannula handle 30 contains a valve not shown which may be opened and closed so that gases may be inserted through the cannula 32 into the abdominal cavity to inflate the abdominal cavity, at insertion. When obturator 22 has opened the valve, the lever 80 on cannula handle 30 moves from its position as in FIG. 1 to its position as in FIG. 2, upon insertion of the obturator 22 into the cannula 32.

As seen in FIG. 2, the obturator tip 23 is exposed after full insertion of the obturator 22 and shield 24 within the cannula 32 in cannula handle 30. A grasping mechanism 40, better seen in FIG. 1, has caused the obturator handle 20 to become firmly attached to the cannula handle. When this occurs, the tip 23 is exposed through the contoured opening of the shield 24, as better seen in FIG. 3. Both the end of the shield and the obturator tip 24 are extended from the end of the cannula 32, also seen in a bottom view of the trocar 10, as in FIG. 4. Thus, the exposed obturator tip 23 can be used to pierce the skin. After piercing, the tip 23 extending from shield 24 and cannula 32 can be used to insert the entire cannula into the abdominal wall. At this time, the abdominal wall becomes anchored by use of anchoring threads 34 contained on the cannula handle 30. The obturator 22 and shield 24 are also readily removable from the cannula 32 by grasping obturator handle 20 and separating it from cannula handle 30.

As better seen in FIG. 5, taken in conjunction with FIG. 1, the shield 24 used to shield the obturator tip 23 is connected to a generally tubular insert 50 which is seen exposed from the outside of the obturator handle 20. The shield 24 is retractable within the obturator handle 30 through opening 31. However, because the shield 24 is spring-loaded by placing spring 35 on insert 50, in a generally relaxed position the shield 24 is made to enclose the obturator tip 23. It is only when the spring 35 is compressed that the obturator tip 23 is exposed.

The usefulness of enclosing the obturator tip 23 is readily apparent. It may be undesirable to have the obturator tip exposed in the operating room or even more importantly, after usage. Thus, the spring 35, either before or after the obturator tip 23 and shield 24 have been removed from the cannula 32, causes the shield 24 to become enclosed over the obturator tip 23. In this way, the obturator tip 23 can be disposed safely.

Although it may be desirable to have the obturator tip 23 enclosed during nonusage, it may also be desirable for the obturator tip 23 to be exposed during times of usage. The current invention allows such practice without any external input from the user. As seen in FIG. 5, the insert 50 attached to the rear of the shield 24 and generally exposed from the obturator handle 30 will generally be placed between the obturator handle 20 and the cannula handle 30. This is more readily seen in FIG. 6.

The insert 50 contains a planar lower surface 51 which will in turn contact the planar upper surface 37 of the cannula handle 30. Because the centrally located tubular opening in the cannula handle is only large enough to accomodate the generally tubular shield 24, the planar surface 51 of insert 50 is not capable of being placed into the opening 38 within the cannula handle 30. Thus, the planar surface 51 is caused to remain located between the opening 31 of the obturator handle 20 and the outside of the cannula handle 30.

When it is desired to affirmatively close the handles upon each other, as seen in FIG. 7, the spring 35 is compressed. Compression of the spring 35 causes retraction of the end 52 of the insert 50 into the obturator handle 20. This is caused generally by force being applied from the cannula handle 30 onto the lower planar surface 51 of the insert 50 connected to the obturator handle 20, until surface 53 contacts opening 31, and retraction is stopped. This in turn causes retraction of the shield 24 into the obturator handle 20 and exposure of the obturator tip 23 from its enclosure within the shield 24. Upon connection of the obturator handle 20 with the cannula handle 30, the obturator tip 23 is caused to be exposed outside the end of the cannula 32. In this way, during the entire usage period of the trocar 10, the obturator 22 is exposed and the problems previously encountered with pneumoperitoneal tenting are avoided.

In usage the steps of puncturing and inflating the internal portion of the abdominal cavity are as follows. First, the user takes a shielded obturator 22 and places it within a open cannula 32 of compatible size. Second, the user intentionally closes the cannula handle 30 upon the obturator handle 20. This in turn exposes the obturator tip 23 from outside the end of the cannula 32. The user then punctures the abdominal wall with the exposed obturator tip 23. After puncturing, for which pneumoperitoneal tenting is now non-existent, the obturator 22 and shield 24 "attached to obturator handle 20" are removed from the cannula 32 attached to cannula handle 30 by separating obturator handle 20 and cannula handle 30 and sliding obturator 22 and shield 24 out of cannula 32, to separate these pieces, much as seen in FIG. 1. The user simply grasps locking mechanism 40 by placing his fingers on grasps 42 in a squeezing motion, and exerts enough pinching force so that the grasps 42 from mechanism 40 release from cannula handle 30. Thereafter, obturator handle 20 can be removed from cannula handle 30, leaving cannula 32 within the abdomen.

Upon removal, the previously compressed spring 35 now relaxes, so that the shield 24 is caused to cover the obturator tip 23. Thus, upon removal the obturator tip 23 is again enclosed and its removal and disposal is safe to the user. The cannula 32 is now firmly emplaced within the abdominal cavity and laparoscopic procedures can continue. Upon completion of such procedures, the cannula 32 can be removed and discarded as it has been made separate from the obturator 22 and shield 24.

What is claimed is:
1. A trocar assembly comprising:
an obturator connected to an obturator handle;
a shield surrounding said obturator, and movable relative to said obturator handle, and a spring maintaining said obturator in a shielded position with said shield surrounding said obturator;
a cannula connected to a cannula handle, said obturator and shield insertable into said cannula such that said cannula handle and said obturator handle come into contact; and insert means emplaceable between said cannula handle and said obturator handle, wherein when said obturator is placed into said cannula said insert means retracts said shield to expose said obturator tip from said shield at all times when said handles come into contact.

2. The assembly of claim 1 wherein said obturator, cannula and shield are tubular in shape.

3. The assembly of claim 1 wherein said actuating means comprises an insert attached to said shield.

4. The assembly of claim 3 wherein said insert is emplaced between said obturator handle and said cannula handle.

5. The assembly of claim 4 wherein said shield is spring loaded within said obturator handle.

6. A trocar assembly comprising:
   a shield and an obturator having a sharpened tip and both said shield and obturator connected to an obturator handle, such that said shield is retractable into said obturator handle;
   a cannula handle and a cannula connected to said cannula handle, said shield and obturator insertable into said cannula; and
   actuating means attached to said shield and actuable by said cannula handle, said actuating means retracting said shield into said obturator handle to expose said tip upon contact of said actuating means and said cannula handle.

7. A method of puncturing skin, comprising:
   a. providing an obturator handle and a shield and an obturator with a sharpened tip, said shield and obturator connected to said obturator handle and said shield capable of covering said tip;
   b. providing a hollow cannula and cannula handle, said cannula connected to said cannula handle;
   c. placing said shield and obturator into said cannula;
   d. actuating said shield to expose said tip, said actuation taking place at all times during contact between said handles; and
   e. using said tip to puncture the skin.

* * * * *